March. 12, 1974 H. HOLTKAMP Plant Pat. 3,511
AFRICAN VIOLET
Filed Aug. 24, 1972
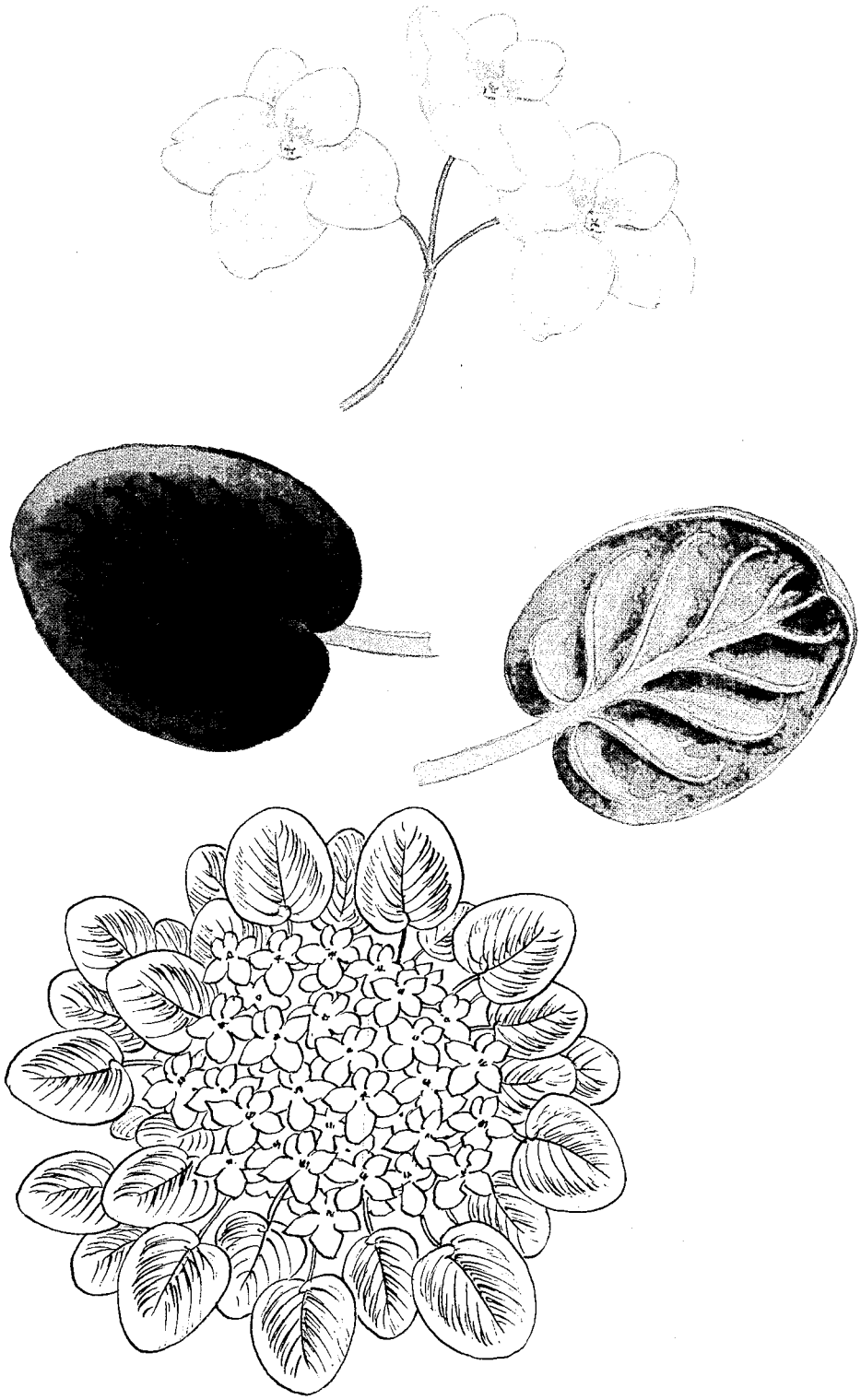

United States Patent Office

Plant Pat. 3,511
Patented Mar. 12, 1974

3,511

AFRICAN VIOLET

Hermann Holtkamp, Werther Strasse 5–7, Postfach 19, 4243 Isselburg, Germany

Filed Aug. 24, 1972, Ser. No. 283,369
Int. Cl. A01h 5/00
U.S. Cl. Plt.—69 1 Claim

ABSTRACT OF THE DISCLOSURE

A hybrid violet of a descendant of a cross between *Saintpaulia ionantha* and *Saintpaulia shumensis* species which has permanent characteristics including strength of stem, fast and vigorous growth, profuse flowering, uniform bouquet, prolonged blooming period, resistance to disease, reliability in initiating new plantlets, retention of flowers past maturity on their respective stems, and uniformity throughout the life cycle.

The present new variety is a sport of the "Rhapsodie" Violetta variety disclosed in my United States Letters Patent No. PP 3,241 of July 25, 1972, having substantially the same characteristics as the parent plant as described in said patent, except for the color of the flowers, which is a very light pinkish orchid, with striates of darker orchid at center.

Asexual reproduction of my new variety by leaf-cuttings, as performed by me at Isselburg, Rhineland, Germany, shows that the foregoing characteristics and distinctions come true to form and are established and transmitted through succeeding propagations.

DESCRIPTION OF DRAWINGS

The upper illustrations show, in full color, a cluster of flowers on one of the petioles from a stem, and the opposite sides of one of the leaves; and below, in pen and ink, a top plan view in reduced size of a plant showing a flower head and a wreath of leaves therearound.

DETAILED DESCRIPTION

The present variety is a sport of "Rhapsodie" Violetta Type 12/802 which is fully described in the above Letters Patent.

Name: "Rhapsodie" Caroline
Parent: "Rhapsodie" Violetta Type 12/802
Leaves: Borne in rosette arrangement around a central flower head
Flowers: Borne profusely in a large central flower head which is approximately from five to six inches in diameter at second blooming and approximately 25–35 flowers per stem at full maturity Individual flowers: Quinquepartite, bilaterally symmetrical
*Size.*—1 to 1¼ inches in diameter
*Color.*—Light orchard with darker orchid center
*Calyx.*—Quinquepartite
*Peduncles.*—Multiflorous, up to 4 inches long, borne in compact cymes with 8–14 flowers at second blooming The following color designations are according to "Dictionary of Color" by Maerz and Paul:

| | Plate Letter | No. |
|---|---|---|
| Main body of flower—light orchid: | | |
| Main body of petals | 42 B | 3 |
| Small petals at anthers | 42 J | 6 |
| Anthers—light yellow | 9 L | 1 |

GENERAL CHARACTERISTICS

While there may be minor variations in the leaf size, shape and color, and in the shape of the flowers, which are common to African violets, there is substantial uniformity in all the other characteristics described in the aforesaid patent.

Thus in the present variety, the characteristics that are constant and that distinguish it from the other varieties include: (a) the large central flower head of from approximately five to six inches in diameter at second blooming, the flowers of which are of light orchid color with a darker color adjacent the anthers, and (b) the wreath or collar of dark green leaves surrounding the flower head of the color described.

The flower head itself contains from six to eight stems at first blooming with approximately six blooms on each stem at first blooming and approximately double that number at second blooming.

In the present variety three large petals are at one side of the central bright yellow anthers, and two smaller petals are at the opposite side. The deeper central orchid color appears most prominent on the two smaller petals.

I claim:

1. A distinct variety of African violet substantially as herein shown and described, characterized by a habit of bearing a large, central flower head of approximately five to six inches in diameter at second blooming supporting the flowers of each flower head above a wreath of dark green leaves, which flowers have petals of a distinctive and attractive light orchid color deepening to a deeper orchid color adjacent the central bright yellow anthers in the smaller of said petals.

No references cited.

ROBERT E. BAGWILL, Primary Examiner